United States Patent [19]

Bastyr et al.

[11] Patent Number: 5,520,622
[45] Date of Patent: May 28, 1996

[54] ORTHOPEDIC BRACE HAVING A PNEUMATIC PAD AND ASSOCIATED PUMP

[75] Inventors: Charles A. Bastyr, San Diego; Richard E. Gildersleeve, Escondido; Theodore V. Tillinghast, III, Cardiff; Keith L. Cassford, San Diego, all of Calif.

[73] Assignee: Smith & Nephew Donjoy Inc., Carlsbad, Calif.

[21] Appl. No.: 251,858

[22] Filed: May 31, 1994

Related U.S. Application Data

[63] Continuation-in-part of Ser. No. 907,160, Jul. 1, 1992, Pat. No. 5,316,547, Ser. No. 104,184, Aug. 10, 1993, Ser. No. 191,410, Feb. 3, 1994, Ser. No. 199,091, Feb. 22, 1994, and Ser. No. 246,972, May 19, 1994, which is a continuation-in-part of Ser. No. 104,184, and Ser. No. 907,160, said Ser. No. 104,184, is a continuation-in-part of Ser. No. 907,160, said Ser. No. 191,140, is a continuation-in-part of Ser. No. 104,184, said Ser. No. 199,091, is a continuation-in-part of Ser. No. 104,184, and Ser. No. 907,160.

[51] Int. Cl.$^6$ ..................................................... A61F 5/00
[52] U.S. Cl. ................... 602/16; 602/13; 602/26
[58] Field of Search .................................. 602/5, 13, 16, 602/23, 26

[56] References Cited

U.S. PATENT DOCUMENTS

| | | |
|---|---|---|
| 2,531,074 | 11/1950 | Miller .......................... 128/DIG. 20 X |
| 3,581,741 | 6/1971 | Rosman ................................ 602/26 X |
| 3,902,482 | 9/1975 | Taylor . |
| 3,945,047 | 3/1976 | Jarrell, Jr. . |
| 3,955,565 | 5/1976 | Johnson, Jr. . |
| 3,958,569 | 5/1976 | Vosburgh . |
| 4,201,203 | 5/1980 | Applegate ................................ 602/26 |
| 4,219,892 | 7/1980 | Rigdon ................................ 602/26 X |
| 4,280,489 | 7/1981 | Johnson, Jr. . |
| 4,287,920 | 9/1981 | Johnson, Jr. . |
| 4,378,009 | 3/1983 | Rowley et al. . |
| 4,567,887 | 2/1986 | Couch, Jr. ............................. 602/13 X |
| 4,624,247 | 11/1986 | Ford . |
| 4,628,954 | 12/1988 | Johnson, Jr. . |
| 4,632,098 | 12/1986 | Grundei et al. . |
| 4,634,176 | 2/1987 | Mason et al. . |
| 4,667,672 | 5/1987 | Romanowski .............. 128/DIG. 20 X |
| 4,703,750 | 11/1987 | Sebastian et al. ........................ 602/13 |
| 4,777,946 | 10/1988 | Watanabe et al. . |
| 4,821,707 | 4/1989 | Audette . |
| 4,870,956 | 10/1989 | Fatool et al. . |
| 4,872,448 | 10/1989 | Johnson, Jr. . |
| 4,938,207 | 7/1990 | Vargo . |
| 4,999,932 | 3/1991 | Grim . |
| 5,002,045 | 3/1991 | Spademan . |
| 5,022,391 | 6/1991 | Weidenburner . |
| 5,025,575 | 6/1991 | Lakic . |
| 5,025,782 | 6/1991 | Salerno . |
| 5,042,464 | 8/1991 | Skwor et al. . |
| 5,078,128 | 1/1992 | Grim et al. . |
| 5,088,478 | 2/1992 | Grim . |

(List continued on next page.)

FOREIGN PATENT DOCUMENTS 2136294   9/1984   United Kingdom .............. A61F 5/01

OTHER PUBLICATIONS

Generation II Orthotics USA Inc., *Osteoarthritis Pain–Free Mobility*, 1993, USA.

Omni Scientific, Inc., *Radiograph Engineered Custom Bracing*, 1993, USA.

Primary Examiner—Linda C. Dvorak
Attorney, Agent, or Firm—Brown, Martin, Haller & McClain

[57] ABSTRACT

A hinged orthopedic knee brace has a structural frame made up of a plurality of rigid or stiffened support components dynamically connected by one or more hinges. A plurality of pneumatic pads are attached to the inside faces of the frame to effectively grip the body of the user and simultaneously cushion the body from the frame. Each pad is connected in selective fluid communication with a pump and a fluid release valve enabling the user to instantaneously inflate or deflate the pads whenever desired to enhance the fit of the brace on the body of the user.

5 Claims, 6 Drawing Sheets

U.S. PATENT DOCUMENTS

| | | | |
|---|---|---|---|
| 5,107,823 | 4/1992 | Fratesi | 602/26 X |
| 5,113,599 | 5/1992 | Cohen et al. | |
| 5,125,400 | 6/1992 | Johnson, Jr. | |
| 5,125,700 | 6/1992 | Johnson, Jr. | 602/13 |
| 5,158,767 | 10/1992 | Cohen et al. | |
| 5,186,163 | 2/1993 | Dye | |
| 5,230,695 | 7/1993 | Silver et al. | 602/13 |
| 5,277,698 | 1/1994 | Taylor | |
| 5,360,394 | 11/1994 | Christensen | 602/13 X |

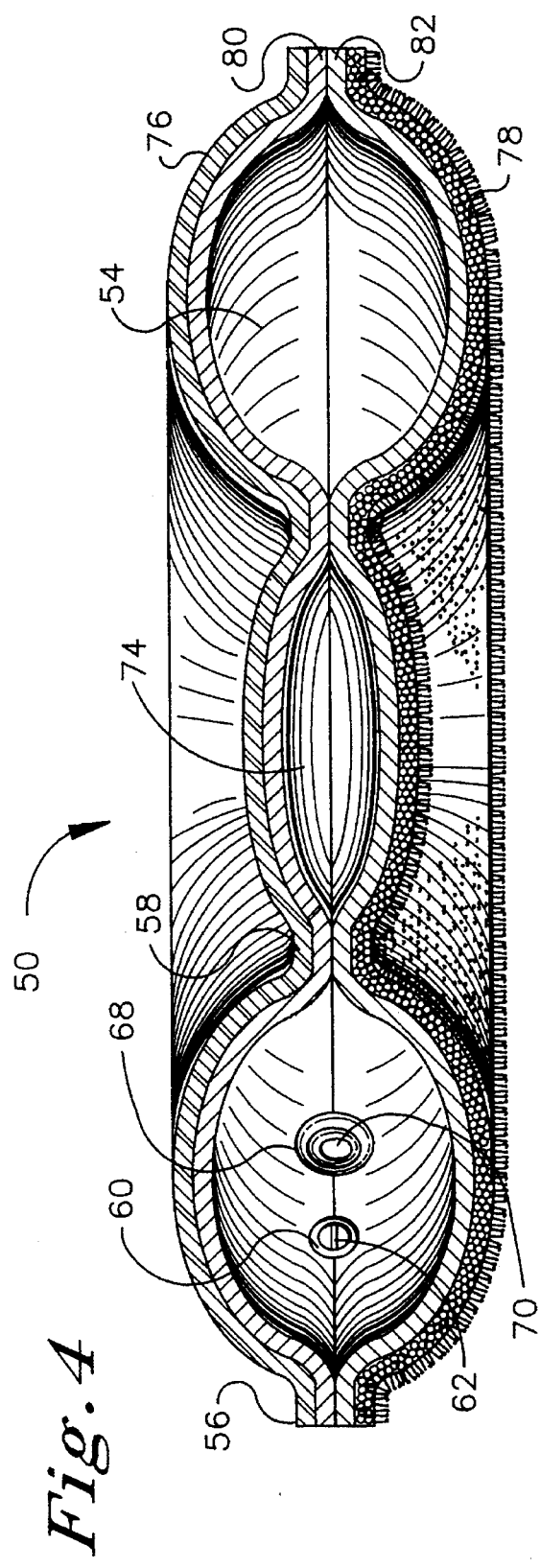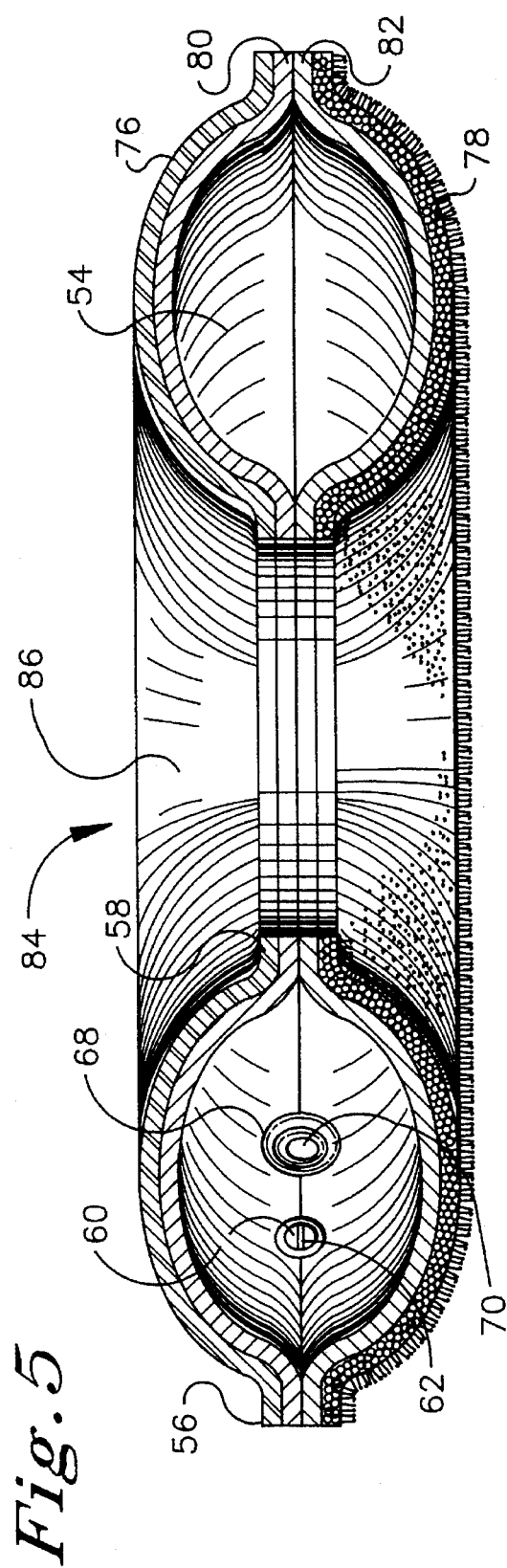

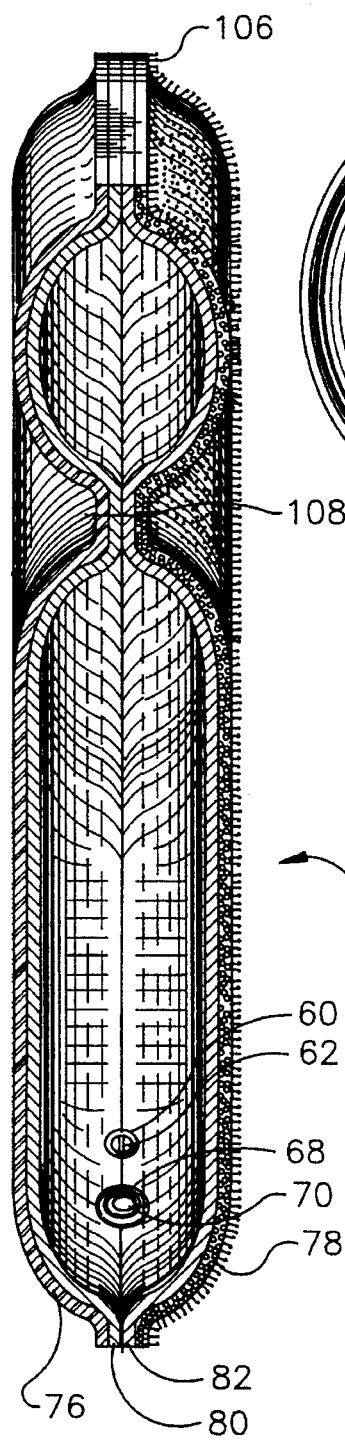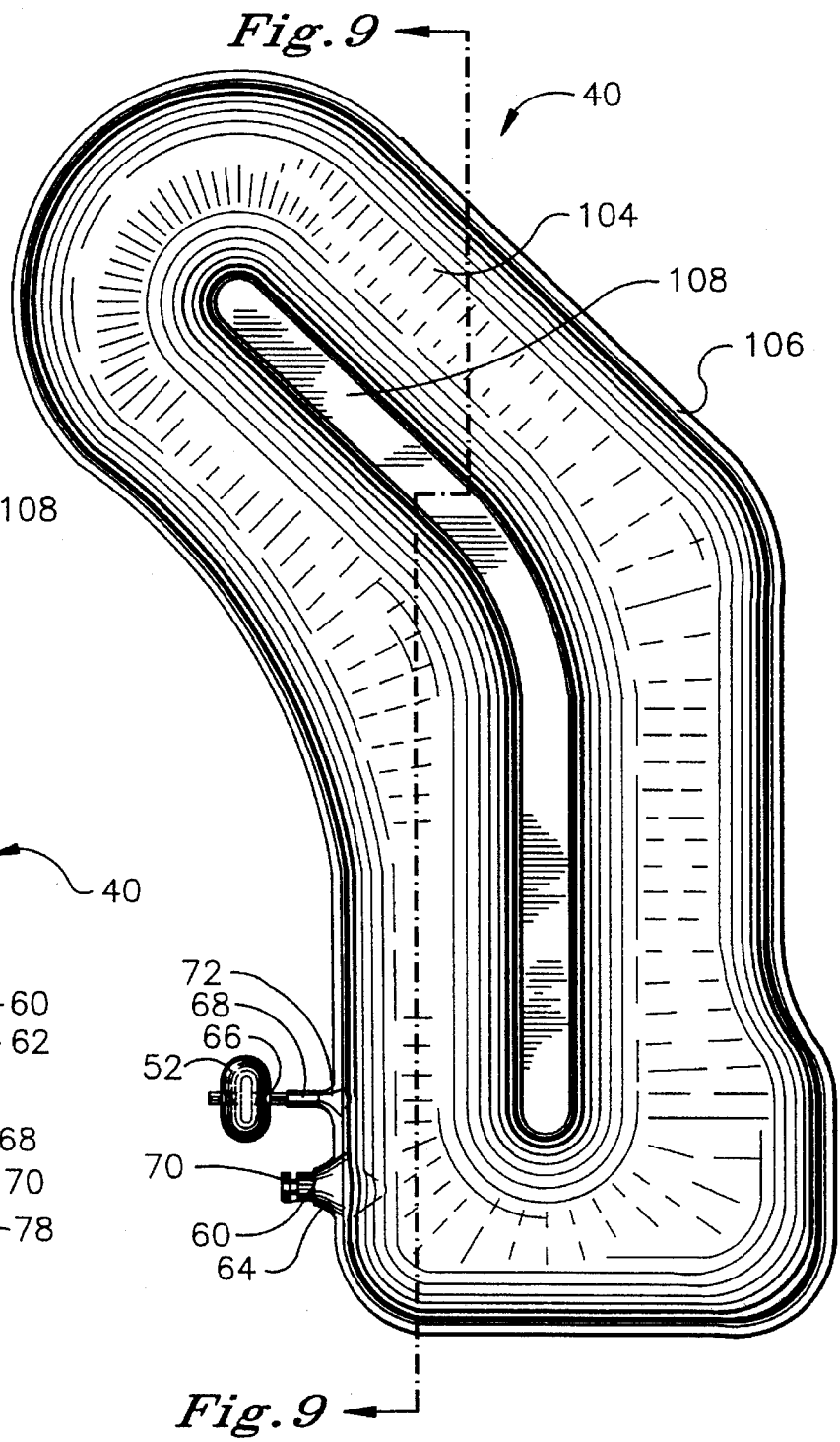

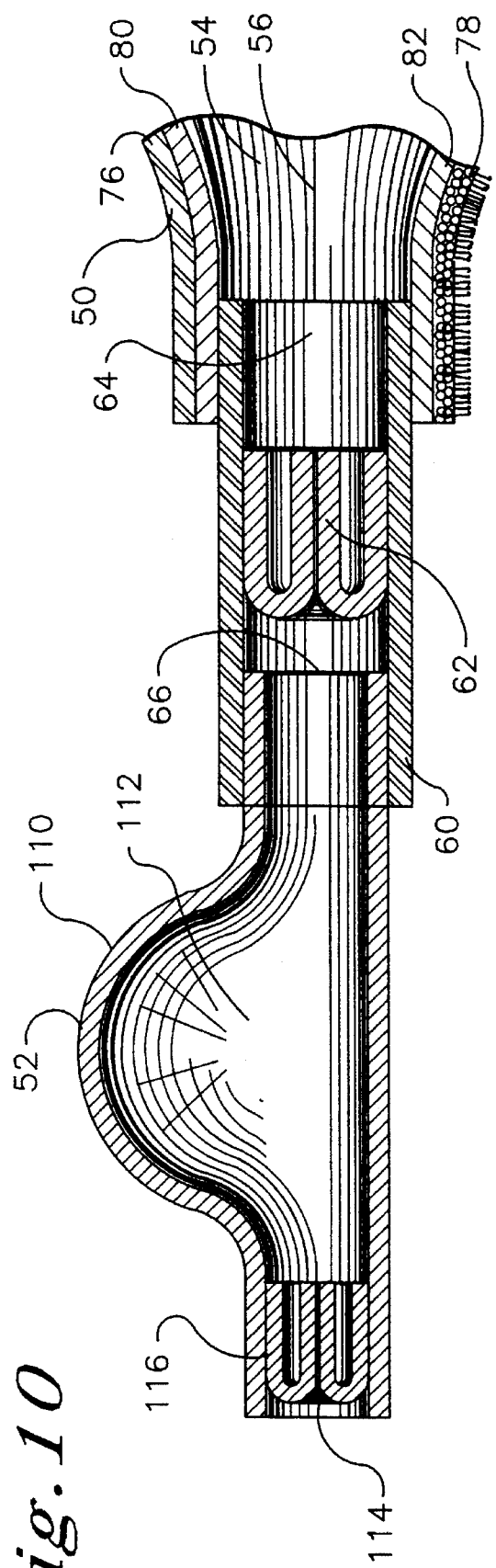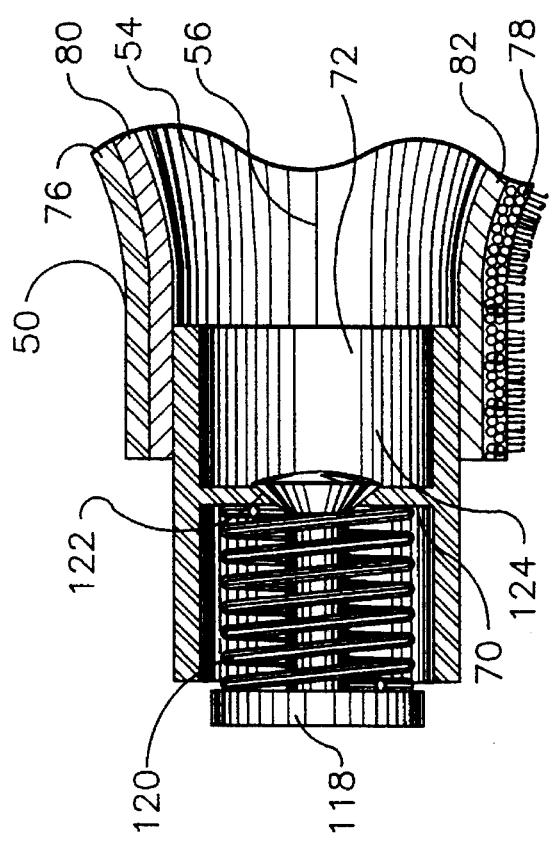

ORTHOPEDIC BRACE HAVING A PNEUMATIC PAD AND ASSOCIATED PUMP

This patent application is a continuation-in-part patent application of the following co-pending patent applications:

| Serial Number | Filing Date |
|---|---|
| 07/907,160 (Issued May 31, 1994 as U.S. Pat. No. 5,316,547) | July 1, 1992 |
| 08/104,184 | August 10, 1993 |
| 08/191,410 | February 3, 1994 |
| 08/199,091 | February 22, 1994 |
| 08/246,972 | May 19, 1994 |

Ser. No. 08/104,184 is a continuation-in-part of Ser. No. 07/907,160. Ser. No. 08/191,410 is a continuation-in-part of Ser. No. 08/104,184. Ser. No. 08/199,091 is a continuation-in-part of Ser. Nos. 08/104,184 and 07/907,160. Ser. No. 08/246,972, is a continuation-in-part of Ser. Nos. 08/104,184 and 07/907,160.

TECHNICAL FIELD

The present invention relates to an orthopedic brace, and particularly to an orthopedic brace having a pneumatic pad and associated pump attachable to the brace for adjustably fitting the brace against the body of a user.

BACKGROUND OF THE INVENTION

Hinged orthopedic braces are commonly employed to stabilize a skeletal joint of a user when the joint has been weakened by injury or other infirmity. The brace typically has a structural frame that is made up of a plurality of rigid or stiffened support components dynamically linked together by one or more hinges to support the joint during user activity. The frame is mounted on the body of a user such that the hinges traverse the joint being stabilized, while the support components are secured to the body by a system of pliant straps. Solid elastomeric pads or fluid-filled pneumatic pads are attached to the inside of the frame to cushion the user's body from the frame and provide a stable base of support for the frame against the user's body.

Despite such pads, the user frequently experiences discomfort from painful point loads while wearing a closely-fitted brace because of the high forces the brace applies to the body during routine or rehabilitative physical activity. The discomfort is attributable to improper compression characteristics in conjunction with improper sizing and configuration of the pads. Known pads are generally not configured in conformance with the structure of the brace and the contours of the body. Furthermore known pads are not readily adaptable to transient changes that body tissue undergoes, such as swelling or shrinkage, during routine or rehabilitative physical activity.

Elastomeric or pneumatic pads configured in conformance with the patella have been utilized in pliant or "soft" knee braces. U.S. Pat. Nos. 4,201,203 and 4,777,946 disclose soft knee braces having an elastomeric patella pad. U.S. Pat. Nos. 4,378,009 and 4,938,207 disclose soft knee braces having inflatable pneumatic patella pads. Pneumatic pads adequately conformed to the body, however, have not been utilized in hinged orthopedic braces having rigid or stiffened frames. U.S. Pat. No. 5,125,400 discloses an orthopedic brace having inflatable pneumatic pads positioned between the ankle of the user and the rigid support components of the brace. U.S. Pat. No. 5,107,823 discloses a thigh guard having an inflatable pneumatic pad positioned between the thigh and a rigid protective shell. In both instances, however, the pads are not significantly configured in conformance with the corresponding body contours.

Some hinged orthopedic braces have specifically addressed the problem of closely fitting the rigid frame of the brace with the knee or elbow joint of the body while simultaneously cushioning the body from the rigid frame. French patent publication FR 2627-381-A discloses a brace having a pair of disk-shaped fluid-filled pads positioned on the frame of the brace to abut the knee or elbow condyles. U.S. Pat. No. 3,581,741 discloses a brace having a doughnut-shaped solid felt or rubber pad positioned between the rigid frame of the brace and the medial meniscus of the knee. Yet, the art does not disclose pneumatic pads configured in substantial conformance with the contours of the user's body for use with hinged orthopedic braces having rigid or stiffened frames.

Accordingly, it is an object of the present invention to provide an orthopedic brace having a rigid or stiffened structural frame that can be secured to the body of a user with both a high degree of stable support and a high degree of user comfort. It is a further object of the present invention to provide a lightweight pneumatic pad attachable to the frame of an orthopedic brace that comfortably stabilizes the frame against the body of the user by dynamically conforming to and firmly gripping the contours of the body while fully cushioning the body contours from the rigid or stiffened support components of the frame. It is yet another object of the present invention to provide a pump associated with the pad to facilitate selective inflation of the pad when desired, thereby enhancing the comfort of the user and the stability of the frame against the body.

It is another object of the present invention to provide an off-the-shelf orthopedic brace that can be adapted to fit the body contours of any number of users. It is another object of the present invention to provide a custom orthopedic brace that is readily configured to changing body contours of a specific individual user. It is still another object of the present invention to provide an orthopedic brace having a fit that can be instantaneously adapted to the requirements of different activities by the user. It is a further object of the present invention to provide an orthopedic brace having a fit that can be instantaneously adjusted to transient conditions of the body such as localized tissue swelling or shrinkage.

SUMMARY OF THE INVENTION

In accordance with one embodiment, the present invention is a hinged orthopedic brace having a structural frame, at least one pneumatic pad engaging the frame, and a pump in fluid communication with the pneumatic pad. The frame comprises a plurality of rigid or stiffened support components and a hinge dynamically connecting the support components. The pneumatic pad comprises a fluid-containing bladder formed from a flexible skin that is shaped into a containment configuration to enclose a quantity of fluid therein. The pneumatic pad provides secure and comfortable support for the brace when the frame is mounted on the body of a user.

The degree of support the pneumatic pad provides the brace is adjustable by the selective addition of fluid to the bladder or the selective release of fluid from the bladder. Accordingly, the bladder is provided with means for such selective addition and release of fluid. The selective fluid addition and release means, in accordance with a preferred embodiment of the present invention, is a pair of fluid ports. One port is a fluid-addition port providing a bladder inlet in fluid communication with the pump that is adapted to enable the selective addition of fluid to the bladder. The other port is a fluid-release port providing a bladder outlet in fluid communication with the external environment that is adapted to enable the selective release of fluid from the bladder.

The pump is substantially any fluid drive means in fluid communication with the bladder for injecting fluid therein. A preferred pump is a manually-powered mechanism for driving ambient air from the external environment into the bladder. Such a pump includes an elastic bulb enclosing a pump chamber inflatable with air. The bulb is formed from a compressible elastomeric material exhibiting good memory characteristics. The bulb has a pump inlet selectively providing fluid communication between the pump chamber and an external environment of ambient air. The bulb also has a pump outlet selectively providing fluid communication between the pump chamber and the bladder inlet. A one-way injection valve is provided downstream of the pump chamber to permit air flow between the chamber and bladder only in the direction of the bladder. A release valve is also provided at the bladder outlet to enable the selective release of pressurized air from the bladder to the external environment as desired by the user.

With the brace in place on the body of a user, the thickness of the pneumatic pad or the corresponding air pressure therein is systematically adjustable by inflating or deflating the bladder of the pad as desired to closely fit the structural frame of the brace with the specific contours of the body of the user. The pneumatic pad permits the user to instantaneously adapt the fit of the frame to different user activities or to changing conditions of the user's body. Thus, for example, if swelling is experienced by the user, the bladder can be deflated by the release of fluid therefrom to reduce the thickness or air pressure of the pad, thereby reducing the pressure of the brace on the body of the user and enhancing the comfort of the user. In contrast, if undesirable movement of the brace is experienced relative to the body of the user during vigorous physical activity, the user can inflate the bladder by the addition of fluid thereto to increase the thickness or air pressure of the pad, thereby increasing the pressure of the brace on the body of the user and providing a tighter fit of the frame to the body.

Fluid addition to the bladder is effectuated by cycling the pump through an intake mode and a discharge mode while maintaining the release valve at the fluid-release port closed. During the intake mode the bulb is inflated by elastic expansion, while maintaining the injection valve at the fluid-addition port closed. Inflation draws air under ambient pressure from the external environment into the pump chamber via the pump inlet. During the discharge mode the pump inlet is closed and the bulb is deflated by compression. Deflation urges air at elevated pressure against the injection valve causing the valve to open. The air consequently flows from the pump chamber into the bladder via the pump outlet and bladder inlet. Fluid release is effectuated simply by opening the release valve at the fluid-release port, thereby allowing the pressurized air in the bladder to flow into the external environment at a lower ambient pressure via the bladder outlet.

It is readily apparent to the skilled artisan that alternate configurations of the above-described pump and bladder inlets and outlets are possible within the scope of the present invention by appropriately modifying the port and valving configuration of the bladder and pump. For example, the selective addition and release means for the bladder can be integrally contained within a single unitary port, rather than within separate fluid-addition and fluid-release ports. The single port alternately serves as either the bladder inlet or bladder outlet depending on the selective setting of a valve provided at the port that is adapted to alternately enable fluid addition to the bladder and fluid release from the bladder. By providing appropriate valving within the purview of the skilled artisan, the pump outlet, in concert with the pump inlet, can selectively function as the bladder outlet to enable the present configuration.

The above-described embodiment of a hinged orthopedic brace and its alternate configurations are particularly applicable to a hinged orthopedic knee brace mountable on the leg of a user to stabilize the knee joint by restricting the motion thereof. The orthopedic knee brace comprises a structural frame made up of a hinge and a plurality of substantially rigid or stiffened upper and lower support components. The upper support components are engagable with the upper leg above the knee joint and the lower support components are engagable with the lower leg below the knee joint. The hinge is positionable at the knee joint and rotatably connects the upper and lower support components to pivot them about the hinge in correspondence with flexion and extension of the knee joint as permitted by setting the rotation range of the hinge.

The present orthopedic knee brace further comprises a pneumatic knee condyle pad, a plurality of pneumatic upper and lower support pads, and one or more pumps in fluid communication with the condyle and support pads enabling inflation thereof. The knee condyle pad is attached to the inside face of the hinge, providing a stable base of support for the brace against the knee of the user. The knee condyle pad also cushions the lateral or medial knee condyle from the hinge or other proximate support components of the frame and diminishes point loads to the knee condyle when the brace is mounted on the leg of the user. The upper and lower support pads are attached to the inside faces of the upper and lower support components, respectively, enhancing the base of support for the brace against the upper and lower legs of the user. The support pads also cushion the upper and lower legs from the upper and lower support components of the frame, respectively, and diminish point loads to the upper and lower legs when the brace is mounted on the leg of the user. Separate pumps can be attached directly to the bladder inlet of each pad or integrally formed therewith, providing each pad with its own exclusive pump for selective adjustment of the pad. Alternatively, each of the one or more pumps can be in selective fluid communication with a plurality of pads by means of a network of valves and tubing, thereby enabling selective adjustment of a plurality of pads with a single pump.

In another embodiment, the present invention is a pneumatic padding assembly comprising a pump and a specifically configured pneumatic knee condyle pad that is in fluid communication with the pump and is attachable to the above-described structural frame of an orthopedic knee brace. The pneumatic knee condyle pad is a fluid-containing bladder configured to conform to the inside face of the hinge and to the surface of the body overlying the lateral or medial knee condyle. Accordingly, the bladder has a loop configuration with an interior opening. The bladder is sized such that it circumscribes the periphery of the condyle and the interior opening is depressed relative to the bladder to receive the apex of the condyle. The interior opening has a number of alternate configurations including a void space, a continuous sheet of a planar material or a secondary bladder having a considerably smaller volume than the loop-configured bladder.

The loop-configured bladder is a closed curve, having the interior opening positioned either substantially at the center of the bladder or centrally offset toward the distal portion of the bladder. Alternatively, the loop-configured bladder is a partially opened curve having, in addition to the interior opening, a peripheral opening positioned in the distal portion of the bladder that is continuous with the interior opening. The partially opened-curve or centrally offset closed-curve configuration of the bladder provides the distal portion of the bladder with a reduced volume and reduced surface area relative to the proximal portion thereof. Accordingly, the distal portion of the bladder avoids excessive pressure, and the pain associated therewith, on the peroneal nerve and fibular head proximal to the lateral knee condyle, while effectively gripping the knee condyle and simultaneously cushioning the knee condyle from the frame.

In yet another embodiment, the present invention is a pneumatic padding assembly comprising a pump and a specifically configured pneumatic upper or lower support pad that is in fluid communication with the pump and is attachable to the above-described structural frame of an orthopedic knee brace. The pneumatic upper or lower support pad is a fluid-containing bladder configured to conform to the inside face of at least a portion of the upper or lower support component of the frame, as well as to a portion of the surface of the upper or lower leg, respectively. Accordingly, the bladder has an elongated configuration with a right-angle bend formed therein. The bladder also has an interior seam formed in alignment with the longitudinal axis of the bladder.

The construct of the condyle and support pads is substantially the same, wherein a first sheet of an elastically deformable skin overlays a second sheet of the skin. The two sheets are peripherally joined together by at least one seam that defines the plan profile of the bladder and seals the interior of the bladder from the external environment. The bladder is provided with one or two selectively sealable ports as described above through the skin that enable selective fluid communication between the bladder and the pump for adding fluid to the bladder and enable selective fluid communication between the bladder and the external environment for releasing fluid from the bladder.

The pad may further be provided with a pliant facing that is affixed to the outside of one sheet and with a pliant backing that is affixed to the outside of the other sheet. The facing provides a soft, absorbent surface for engagement with the user's body and the backing provides added cushion between the bladder and the support components of the frame. The backing is preferably formed from a hook component or a loop component of a conventional fabric hook and loop fastener coupling, with the remaining component of the fabric coupling being positioned on the inside face of the hinge, facilitating removable attachment of the pad to the brace frame.

A preferred pump has a bulb constructed by molding an elastomeric material into the desired shape of the bulb or by joining two sheets of an elastically deformable skin in the manner described above to form the desired shape of the bulb. The bulb can be integrally constructed coextensive with the bladder or can be constructed separate therefrom and integrally connected to the bladder by means of a tubular port providing a substantially permanent sealed connection therebetween.

The present invention will be further understood, both as to its structure and operation, from the accompanying drawings, taken in conjunction with the accompanying description, in which similar reference characters refer to similar parts.

BRIEF DESCRIPTION OF THE DRAWINGS

FIG. 4 is a cross-sectional view of the knee condyle pad of FIG. 3 as seen along line 4—4.

FIG. 5 is a cross-sectional view of an alternate knee condyle pad of the present invention attachable to the knee brace of FIG. 2.

FIG. 8 is a plan view of a support pad of the present invention attachable to the knee brace of FIG. 2.

FIG. 9 is a cross-sectional view of the support pad of FIG. 8 as seen along line 9—9.

FIG. 10 is a cross-sectional view of a pump of the present invention integrally connected to a pad of FIG. 2.

FIG. 11 is a cross-sectional view of a release valve of the present invention integrally connected to a pad of FIG. 2.

DESCRIPTION OF PREFERRED EMBODIMENTS

Figure 1:
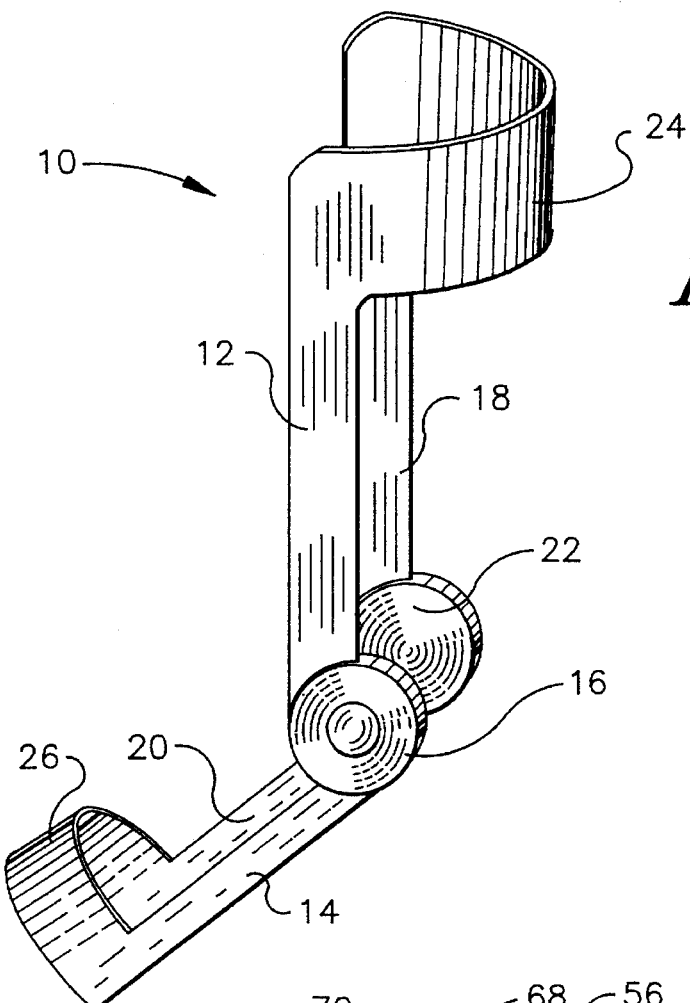
FIG. 1 is a perspective view of a structural frame for a knee brace of the present invention.

Referring initially to FIG. 1, an orthopedic knee brace is shown by way of example, it being understood that the present invention applies generally to orthopedic braces mountable on numerous joints of the body, wherein the brace has a hinged structural frame formed from rigid or stiffened components. The term "rigid" as used herein refers to a component that is substantially inflexible. The term "stiffened" refers to a component that is only somewhat more flexible than a rigid component and, thus, like the rigid component, is sufficiently stiff to significantly resist flexion when positioned on the body of a user. In either case, both the rigid and stiffened components are capable of causing the user discomfort by contact when positioned directly against the body during periods of prolonged activity.

The orthopedic knee brace shown herein has a structural frame generally designated 10. The frame 10, shown by way of example, is a conventional design having a plurality of rigid or stiffened support components including medial upper and lower arms 12, 14, a medial hinge plate 16, lateral upper and lower arms 18, 20, a lateral hinge plate 22, an upper leg cuff 24, and a lower leg cuff 26. The upper and lower leg cuffs 24, 26 have a curved shape providing them with concave inside faces, while the medial and lateral hinge plates 16, 22, the medial upper and lower arms 12, 14, and the lateral upper and lower arms 18, 20 are generally straighter providing them with relatively flatter inside faces. The upper leg cuff 24 and the lower leg cuff 26 are aligned substantially perpendicular to the upper arms 12, 18 and the lower arms 14, 20, respectively.

In practice, the upper support components 12, 18, 24 can be integrally formed in a unitary structure from a high-strength material, such as a plastic, metal or composite. The lower support components 14, 20, 26 can likewise be integrally formed in a unitary structure from similar materials. The hinge plates 16, 22 are generally defined as the rigid or stiffened portion of the frame 10 integral with or proximal to the rotary hinge mechanism, such as the external housing of the rotary hinge mechanism. Portions of the arms 12, 14, 18, 20 proximal to the hinge mechanism, or other proximal components integrally functioning with the hinge mechanism can also be included within the term "hinge plates" as defined herein. The hinge mechanism (obscured from view by the hinge plates 16, 22) is typically a conventional rigid pivot member, such as a pin or rivet, rotatably engaging an upper or lower support component of the frame 10. The term "hinge" as used herein comprises the entire assembly proximal to the intersection of the upper and lower support components including the hinge plates and hinge mechanism.

Figure 2:
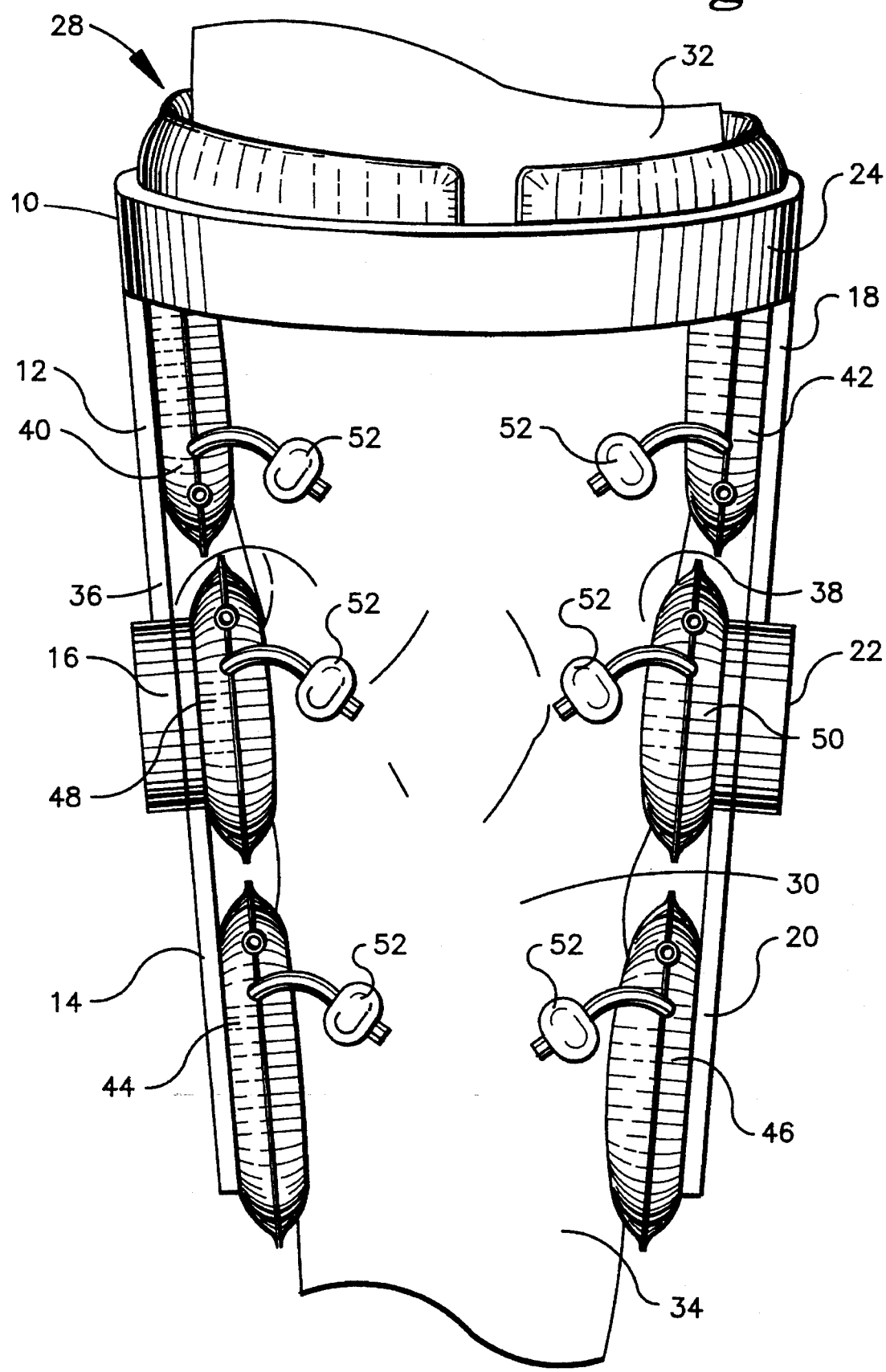
FIG. 2 is a frontal view of the knee brace of the present invention in place on the leg of a user.

Referring to FIG. 2, an orthopedic knee brace of the present invention, having the above-described structural frame 10, is generally designated 28. The knee brace 28 is shown operably positioned on the left leg 30 of a user, wherein the support components of the frame 10 engage the leg 30 at a plurality of contact points. In particular, support of the brace 28 against the leg 30 is provided by engagement of the inside faces of the medial and lateral upper arms 12, 18 and upper leg cuff 24 with the upper leg 32 and engagement of inside faces of the medial and lateral lower arms 14, 20 and lower leg cuff 26 (obscured from view in FIG. 2) with the lower leg 34. Support of the brace 28 against the leg 30 is further provided by engagement of the inside face of the medial hinge plate 16 with the medial knee condyle 36 and engagement of the inside face of the lateral hinge plate 22 with the lateral knee condyle 38.

To facilitate conforming engagement of the frame support components with the leg 30, while simultaneously promoting the comfort of the user, the orthopedic knee brace 28 is provided with a plurality of pneumatic pads that removably attach to the inside faces of the frame 10 at the points of compression contact with the leg 30. In particular, a medial upper support pad 40 is attached to the inside faces of the medial upper arm 12 and upper leg cuff 24. A lateral upper support pad 42, that is substantially a mirror image of the medial upper support pad 40, is attached to the inside faces of the lateral upper arm 18 and upper leg cuff 24. The upper support pads 40, 42 reside in compression between the upper leg 32 and frame 10 when the frame 10 engages the upper leg 32 as shown. Medial and lateral lower support pads 44, 46 substantially similar to the upper support pads 40, 42 are attached to the inside faces of the medial and lateral lower arms 14, 20 and lower leg cuff 26, respectively, to reside in compression between the lower leg 34 and the frame 10 when the frame 10 engages the lower leg 34.

The brace 28 is further provided with pneumatic medial and lateral knee condyle pads 48, 50. The medial knee condyle pad 48 is attached to the inside face of the medial hinge plate 16 to reside in compression between the medial knee condyle 36 and the medial hinge plate 16 when the plate 16 engages the medial knee condyle 36. The lateral knee condyle pad 50 is substantially a mirror image of the medial knee condyle pad 48 and is attached to the inside face of the lateral hinge plate 22 to reside in compression between the lateral knee condyle 38 and the lateral hinge plate 22 when the plate 22 engages the lateral knee condyle 38.

Each pneumatic pad 40, 42, 44, 46, 48, 50 is shown to have a pump 52 associated therewith. More particularly, in accordance with the present embodiment, each pneumatic pad 40, 42, 44, 46, 48, 50 has a pump 52 integrally connected therewith to provide a substantially permanent, sealed fluid passageway between the pump 52 and the respective pneumatic pad. Each pump 52 has substantially the same configuration and construction as is described hereafter. Although not shown in FIG. 2, the brace 28 is also provided with a plurality of adjustable pliant straps engaging the arms 12, 14, 18, 20 and wrapping around the leg 30. The configuration and placement of the straps is conventional and well known to the skilled artisan. The straps secure the frame 10 to the leg 30 of the user by increasing the compression force at the contact points between the frame 10 and leg 30. It is further noted that the present orthopedic knee brace 28 has been described above as positioned on the left leg 30. It is understood by the skilled artisan, however, that the orthopedic knee brace 28 is readily adaptable for positioning on the right leg as well within the scope of the present invention.

Figure 3:
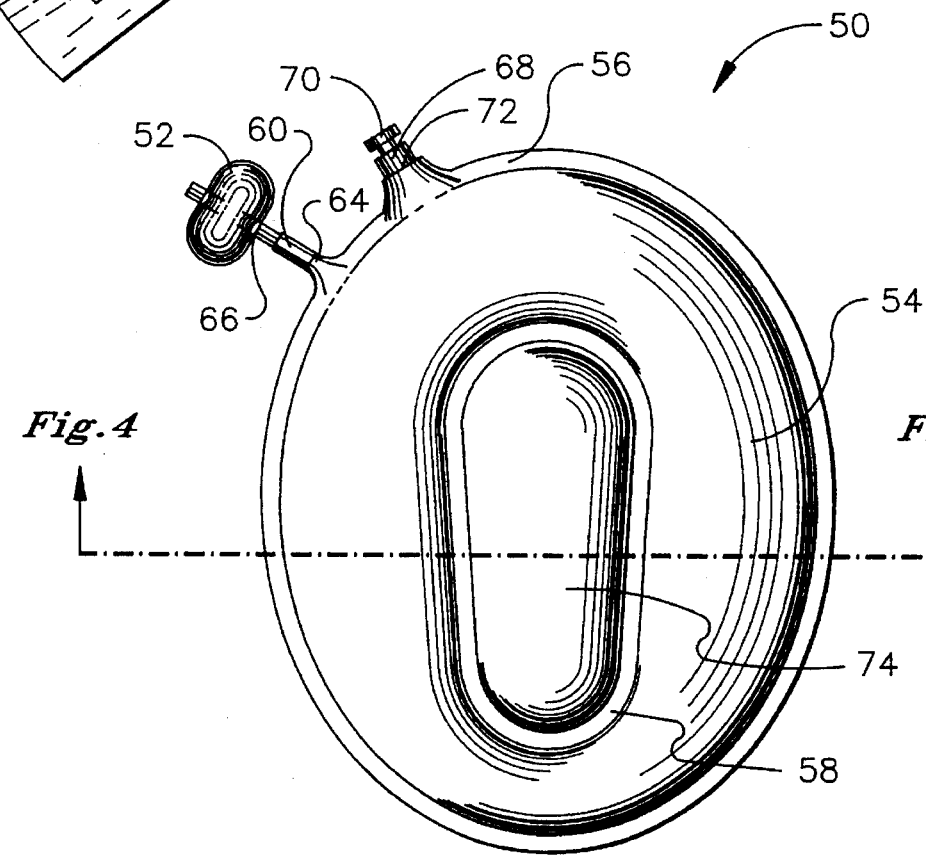
FIG. 3 is a plan view of a knee condyle pad of the present invention attachable to the knee brace of FIG. 2.

The configuration and construction of preferred pneumatic knee condyle pads 48 and 50 are described hereafter with reference to FIGS. 3-7. Referring initially to FIGS. 3 and 4, a first embodiment of a lateral knee condyle pad 50 is shown to comprise a fluid-containing, closed-curve primary bladder 54 having an outer plan perimeter and an inner plan perimeter defined by a primary seam 56 and a secondary seam 58, respectively. The primary seam 56 continuously surrounds the primary bladder 54 following an oval-shaped, closed-loop pathway, thereby defining the entire peripheral outer plan perimeter of the primary bladder 54. The secondary seam 58 also follows a continuous, somewhat oval-shaped, closed-loop pathway and is encircled by the primary seam 56. The secondary seam 58, however, is centrally offset from the primary seam 56. The secondary seam 58 defines the inner plan perimeter of the primary bladder 54 and also defines the outer plan perimeter of an interior opening that is a depression substantially encircled by the primary bladder 54. The interior opening has a number of alternate configurations as described hereafter, but in all cases the interior opening is characterized as having a substantially lesser height or thickness than the primary bladder 54 when the lateral knee condyle pad 50 is not compressed against the body of the user.

The primary and secondary seams 56, 58 are fluid-tight to effectively seal the selected fluid contained within the interior of the primary bladder 54 from the external environment. The fluid contained within the primary bladder 54 is preferably a gas at ambient temperature, such as air. The fluid enables the uncompressed primary bladder 54 to retain a substantially irregular toroid shape. The configuration of the primary bladder 54 is termed "an irregular toroid" because its radial cross-section is not uniform about the entire rotation of the primary bladder 54 due to the off center position of the secondary seam 58.

A tubular fluid-addition port 60 having a one-way injection valve 62 positioned therein is provided having one end extending into the primary bladder 54, and in particular, having one end extending through the primary seam 56 and substantially permanently sealingly engaged thereby, to form a bladder inlet 64. The other end of the tubular fluid-addition port 60 substantially permanently sealingly engages the pump 52 to form a pump outlet 66. The fluid-addition port 60 enables selective fluid communication between the interior of the primary bladder 54 and the interior of the pump 52. Accordingly, when the injection valve 62 is closed, there is substantially no fluid communication between the primary bladder 54 and the pump 52. When the injection valve 62 is opened, fluid communication exists between the primary bladder 54 and pump 52 enabling the addition of fluid to the primary bladder 54 as desired to increase the volume of the primary bladder 54.

A tubular fluid-release port 68 having a release valve 70 positioned therein is also provided having one end extending through the primary seam 56 and substantially permanently sealingly engaged thereby. The other end of the tubular fluid-release port 68 opens to the external environment, forming a selectively openable bladder outlet 72. The fluid-release port 68 enables selective fluid communication between the interior of the primary bladder 54 and the external environment. Accordingly, when the release valve 70 is closed, there is substantially no fluid communication between the primary bladder 54 and external environment. When the release valve 70 is opened, fluid is released from the primary bladder 54 as desired to increase the volume of the primary bladder 54.

As can be appreciated by the skilled artisan, the volume or pressure of the primary bladder 54 is modified to enhance the fit of the brace 28 against the leg 30 or to enhance the cushioning effect of the pad 50. The injection valve 62 is substantially any conventional one-way valve configured to enable fluid flow into, but not out of, the primary bladder 54 via the fluid-addition port 60. The injection valve 62 is preferably a check valve that opens when a sufficient fluid pressure is applied to it from the pump side of the valve, but remains closed when fluid pressure is applied to it from the primary bladder side of the valve. The release valve 70 is substantially any conventional valve permitting fluid flow across it in either direction when open, and permitting substantially no flow across it in either direction when closed. The release valve 70 is preferably a manually operated valve that is spring biased in a closed position.

In accordance with the embodiment of the lateral knee condyle pad 50 shown in FIGS. 3 and 4, the interior opening is occupied by a secondary bladder 74 that is in fluid isolation from the primary bladder 54. The plan perimeter of the secondary bladder 74 is defined by the secondary seam 58 and the secondary bladder 74 has a substantially continuous radial cross section. The secondary bladder 74 contains a lesser quantity of fluid than the primary bladder 54 and is substantially less thick than the primary bladder 54 when the lateral knee condyle pad 50 is not compressed against the body of the user. Unlike the primary bladder 54, the secondary bladder 74 is substantially permanently sealed, having no ports therein, such that the quantity of fluid within the secondary bladder 74 is substantially constant throughout the life of the pad 50.

The primary and secondary seams 56, 58 of the lateral knee condyle pad 50 are configured such that the secondary bladder 74 is centrally offset from the primary bladder 54 toward the distal portion of the pad 50 that is radially opposite the proximal portion of the pad 50. The term "centrally offset" refers to the fact that the primary and secondary bladders 54, 74 do not share a common center. The terms "proximal" and "distal", as used in describing the pad 50, are relative to the midsection of the body of a user on which the orthopedic knee brace 28 is positioned. Accordingly, the plan width of the proximal portion of the primary bladder 54 is substantially greater than the plan width of the distal portion of the primary bladder 54, wherein the plan width is defined as the distance between the outer plan perimeter and the inner plan perimeter of the primary bladder 54, as shown in FIG. 3. Correspondingly, the distal portion of the primary bladder 54 has a substantially reduced volume and surface area relative to the proximal portion of the primary bladder. The present configuration of the lateral knee condyle pad effectively reduces excessive pressure on the peroneal nerve and fibular head, which are in the distal region of the lateral knee condyle 38 shown in FIG. 2.

Specifically referring to FIG. 4, the lateral knee condyle pad 50 is shown to have a laminar construction comprising a facing 76 and a backing 78. It is noted that the thickness of the laminate layers have been exaggerated for purposes of illustration. The facing 76 is a sheet of a soft, pliant, absorbent material, such as synthetic suede or chamois, anteriorly laminated to both the primary and secondary bladders 54, 74. The backing 78 is likewise a sheet of pliant material posteriorly laminated to the bladders 54, 74 in substantially the same manner as the facing 76. A preferred backing 78 is the loop component of a hook and loop fastener, commonly termed VELCRO, configured as a cloth patch. A cloth patch of the hook component (not shown) is similarly laminated to the inside face of the lateral hinge plate 22 opposite the backing 78. It is understood that the positions of the hook and loop components can alternatively be reversed such that the loop component is laminated to the inside face of the lateral hinge plate 22 and the hook component is laminated to the outside of the bladders 54, 74.

In a preferred construction of the lateral knee condyle pad 50, the primary and secondary bladders 54, 74 are shown in FIG. 4 to be integrally formed from two continuous sheets 80, 82 of a film-like skin. The skin is a highly-flexible, elastically-collapsible, fluid-impervious material such as a plastic, e.g., polyurethane or polyvinyl chloride. Construction of the lateral knee condyle pad 50 is initiated by laminating the facing 76 onto the outside of the first sheet 80 and correspondingly laminating the backing 78 onto the outside of the second sheet 82 by an adhesive such as a conventional glue. The bladders 54, 74 are then constructed by overlaying the first sheet 80 atop the second sheet 82. The primary seam 56 is formed by positioning the fluid-addition port 60 and the fluid-release port 68 between the two sheets 80, 82 at the outer plan perimeter thereof and joining the sheets 80, 82 around the ports 60, 68 and along the continuous oval path of the outer plan perimeter using conventional means, such as radio frequency (r.f.) welding. The secondary seam 58 is formed in substantially the same manner as the primary seam 56, but absent the ports, such that the secondary seam 58 is positioned off center from the primary seam 56 and encircled thereby.

It is noted that when the primary and secondary seams 56, 58 are formed, a quantity of fluid, typically ambient air, can be trapped within the interiors of the seams 56, 58. The fluid retained within the interior of the secondary seam 58 remains therein without the further addition or withdrawal of fluid for substantially the life of the pad. The fluid within the interior of the primary seam 56, however, can subsequently be supplemented by injecting additional fluid via the fluid-addition port 60 and injection valve 62 in the manner described above to achieve a desired increase in the thickness or fluid pressure of the primary bladder 54. Consequently, the distance separating the first and second sheets 80, 82 within the primary bladder 54 is substantially greater than the distance of separation within the secondary bladder 74.

Although not shown, the lateral knee condyle pad 50 of FIG. 4 can alternately be configured by evacuating the secondary bladder 74 and laminating the inside of the first sheet 80 to the inside of the second sheet 82 across the entire interior opening. Thus, the secondary bladder is excluded from this embodiment and the interior opening is occupied by the resulting laminate comprising the first and second sheets 80, 82, facing 76, and backing 78.

Referring to FIG. 5, having substantially the same cross-sectional view as FIG. 4, another embodiment of a lateral knee condyle pad is shown and generally designated 84. Identical reference characters are used to identify elements common to both the lateral knee condyle pad 84 and the lateral knee condyle pad 50 insofar as the lateral knee condyle pad 84 is configured substantially the same as the lateral knee condyle pad 50 with the exception of the interior opening. The lateral knee condyle pad 84 excludes the secondary bladder from the interior opening and substitutes an interior void space 86 therefor. Accordingly, the pad 84 contains only one bladder, i.e., the primary bladder 54.

Figure 6:
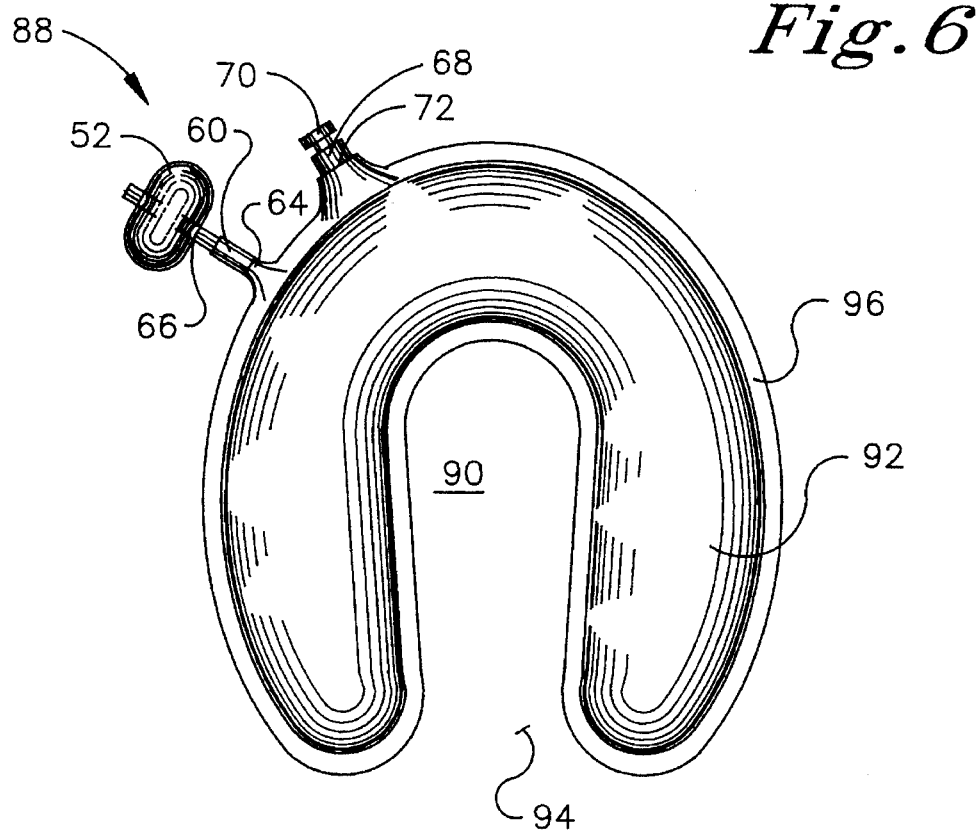
FIG. 6 is a plan view of another alternate knee condyle pad of the present invention attachable to the knee brace of FIG. 2.

Referring to FIG. 6, yet another embodiment of a lateral knee condyle pad is shown and generally designated 88. Identical reference characters are used to identify elements common to the above-described lateral knee condyle pads 50, 84 and the present embodiment of the lateral knee condyle pad 88. Like the lateral knee condyle pad 84, the lateral knee condyle pad 88 excludes the secondary bladder from the interior opening and substitutes an interior void space 90 therefor. The pad 88 also has a primary bladder 92 that is substantially toroid-shaped. The primary bladder 92, however, is a partially opened curve having a relatively limited peripheral opening in the distal portion thereof that is occupied by a peripheral void space 94 continuous with the interior void space 90. Accordingly, the lateral knee condyle pad 88 has a horseshoe-shaped plan perimeter defined by a single close-looped primary seam 96. Because of the peripheral void space 94, the interior void space 90 can be substantially concentric with the primary bladder 92, or alternatively centrally offset therefrom, without defeating the function of the pad 88 to alleviate pressure on the fibular head and peroneal nerve. It is also noted that the lateral knee condyle pad 88 has the same laminar construction as the above-described lateral knee condyle pads 50, 84, comprising two sheets of film-like skin, a facing, and a backing.

Figure 7:
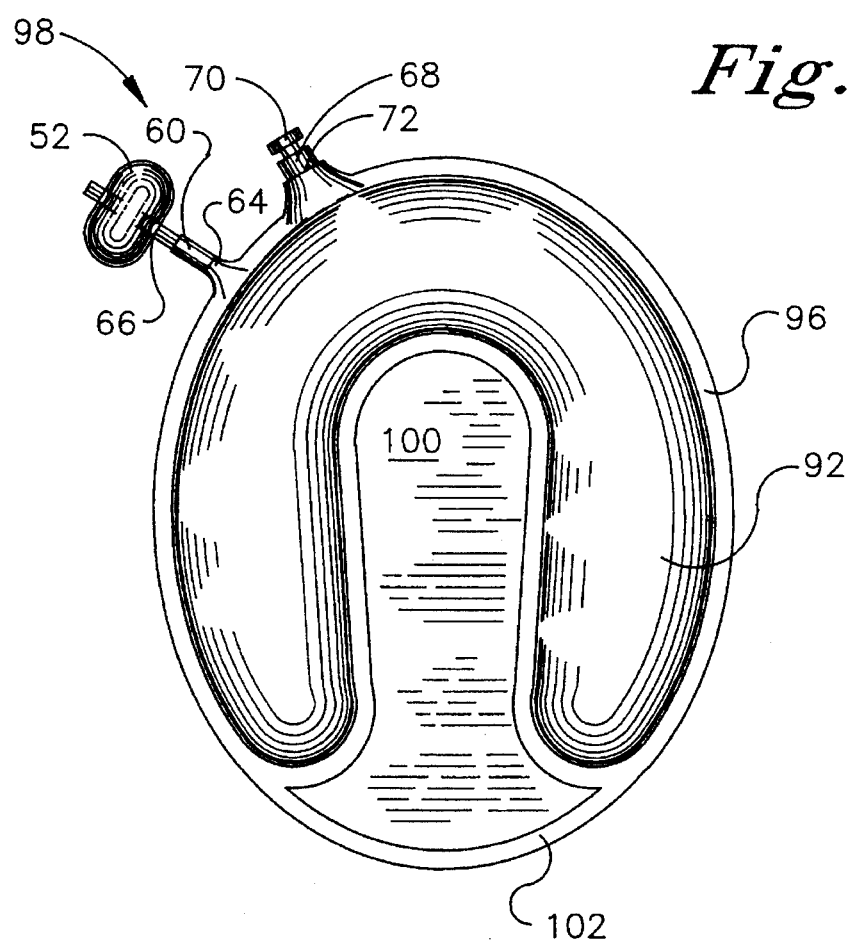
FIG. 7 is a plan view of yet another alternate knee condyle pad of the present invention attachable to the knee brace of FIG. 2.

Referring to FIG. 7, a further embodiment of a lateral knee condyle pad is shown and generally designated 98. Identical reference characters are used to identify elements common to the lateral knee condyle pads 50, 84, 88 and the lateral knee condyle pad 98. The lateral knee condyle pad 98 is configured substantially the same as the lateral knee condyle pad 88 with the exception of the peripheral and interior openings. In addition to the primary bladder 92 and primary seam 96, the lateral knee condyle pad 98 includes a secondary bladder 100 positioned within the peripheral and interior openings thereof and having a similar construction to the secondary bladder 74 of the lateral knee condyle pad 50 shown in FIGS. 3 and 4. The pad 98 also includes a secondary seam 102, extending across the distal plan perimeter of the secondary bladder 100 and having two ends intersecting the primary seam 96.

Although not shown, the lateral knee condyle pad 98 of FIG. 7 can alternately be configured by evacuating the secondary bladder 100 and laminating the insides of the two film-like sheets forming the secondary bladder 100 together across the entire peripheral and interior openings. Thus, the secondary bladder is excluded from this embodiment and the peripheral and interior openings are occupied by the resulting laminate comprising the two film-like sheets, a facing, and a backing.

Although only lateral knee condyle pads have been shown and described above, it is understood that the descriptions of the lateral knee condyle pads apply equally to medial knee condyle pads which are mirror images of the lateral knee condyle pads. It is also understood that other embodiments of knee condyle pads, in addition to those shown and described above, are possible within the scope of the present invention. For example, the present invention encompasses alternate embodiments of knee condyle pads that are substantially identical to the above-described embodiments, but which exclude the facing or backing from the pad.

The present invention further provides for alternate embodiments of knee condyle pads, wherein the primary bladder of the knee condyle pad has a regular toroid shape such that the interior opening is concentric with the primary bladder, as disclosed in U.S. Pat. No. 5,316,547 and U.S. patent application Ser. No. 08/104,184, both incorporated herein by reference. Alternatively, the primary bladder of the knee condyle pad has substantially any shape defining a closed-curve or partially opened-curve loop that conforms to the perimeter of a knee condyle and provides an interior opening for receiving the apex of the knee condyle. In all cases, it is preferred that sufficient fluid is placed in the primary bladder to maintain the height of the primary bladder greater than the height of the knee condyle received therein during use of the brace to prevent substantial compressive contact of the knee condyle with the rigid or stiffened support components of the brace to which the pad is attached. It is further preferred that the primary bladder of the lateral knee condyle pad does not excessively impinge on the fibular head and peroneal nerve in the region of the lateral knee condyle.

Alternative means for producing the knee condyle pad are also provided within the scope of the present invention. For example, the primary bladder can be formed from a single sheet of film-like material, rather than two sheets as disclosed above, by joining the edges of a single sheet together and welding the resulting joint, thus, forming a bladder sealed at the weld or welds. In other production alternatives, the primary bladder may be formed by blow molding or other conventional molding methods available to one skilled in the art.

The configuration and construction of preferred upper and lower support pads 40, 42, 44, 46 are described hereafter with reference to FIGS. 8 and 9. The upper and lower support pads all have a substantially identical configuration and construction. Therefore the upper and lower support pads are described only with reference to the medial upper support pad 40, it being understood that the description applies likewise to the remaining support pads. In addition, identical reference characters are used to identify elements common to both the medial upper support pad 40 and the lateral knee condyle pad 50 insofar as both pads 40, 50 have substantially the same fluid-addition and fluid-release port structures. It is noted that upper and lower support pads having a similar configuration to those shown herein are described in U.S. patent application Ser. No. 08/104,184 and that upper and lower support pads of alternate configuration, but having utility with the brace 28 of the present invention are described in U.S. Pat. No. 5,316,547.

Referring now to FIGS. 8 and 9, the medial upper support pad 40 is shown to include a bladder 104 having a peripheral seam 106 defining the outer plan perimeter of the bladder 104. The configuration of the bladder 104 is characterized as elongate with a substantially right-angle bend along its longitudinal axis. The bladder 104 has an interior seam 108 following at least a substantial portion of the longitudinal axis of the bladder 104 surrounded by, but not intersecting, the peripheral seam 106.

The peripheral seam 106 is fluid-tight to effectively seal the selected fluid contained within the interior of the bladder 104, preferably ambient air, from the external environment. The fluid within the bladder 104 enables the bladder 104 to retain a substantially opened curve tubular shape when the bladder is not compressed against the leg of the user. It is also apparent that when the medial upper support pad 40 is free standing, independent of the stiffened or rigid frame 10, the pad 40 is substantially planar. However, when attached to the medial upper arm 12 and upper leg cuff 24 of the frame 10 as shown in FIG. 2, the medial upper support pad 40 is twistable to a three-dimensional configuration conforming to the frame 10. The conformed medial upper support pad 40 substantially covers the inside face of the medial upper arm 12 and the inside face of a portion of the upper leg cuff 24 corresponding to one quadrant of a circle defined by the upper leg cuff 24. The remaining support pads 42, 44, 46 similarly conform to the inside faces of the respective support members of the frame 10 as shown in FIG. 2.

The presence of the interior seam 108 on the bladder 104 facilitates conformance of the medial upper support pad 40 to the inside face of the frame 10, thereby enhancing the fit of the frame 10 to the upper leg 32. The interior seam 108 also functions to desirably increase the contact interface between the bladder 104 and the frame 10, further enhancing the fit of the frame 10 to the upper leg 32. The interior seam 108 essentially bifurcates the substantially convex, tubular-shaped bladder 104, thereby significantly increasing the contact surface of the medial upper support pad 40 relative to a similar pad configuration absent the interior seam 108.

Like the lateral knee condyle pad 50, the bladder 104 of the medial upper support pad 40 is provided with a tubular fluid-addition port 60 having a one-way injection valve 62 positioned therein. One end of the fluid-addition port 60 extends through the peripheral seam 106 of the bladder 104 to form a bladder inlet 64 and the other end sealingly engages the pump 52 integrally connected with the medial upper support pad 40 to form a pump outlet 66. The bladder 104 is also provided with a tubular fluid-release port 68 having a release valve 70 positioned therein. One end of the fluid-release port extends through the peripheral seam 106 and the other end opens to the external environment, forming a selectively openable bladder outlet 72. The fluid-addition port 60, fluid-release port 68, and associated valves 62, 70 function in substantially the same manner as described above with respect to the lateral knee condyle pad 50, thereby enabling selective fluid communication between the interior of the bladder 104 and the interior of the pump 52 and enabling selective fluid communication between the interior of the bladder 104 and the external environment, respectively.

The medial upper support pad 40 is also constructed in substantially the same manner from the same materials as described above with respect to the lateral knee condyle pad 50. Accordingly, the medial upper support pad 40 has a laminate construction including two sheets 80, 82 of film-like skin, a facing 76, and a backing 78.

The configuration and construction of a preferred pump 52 and release valve 70 is described hereafter with reference to FIGS. 10 and 11. Although the pump 52 and release valve 70 are described in association with the lateral knee condyle pad 50, it is understood that the pump 52 and release valve have utility with any of the above-described pneumatic pads.

The pump 52 and release valve 70 are conventional, being substantially as disclosed in U.S. Pat. No. 5,113,599, incorporated herein by reference. Referring to FIG. 10, the pump 52 comprises a bulb 110 enclosing a pump chamber 112. The bulb 110 is formed from an elastomeric material having good memory characteristics and preferably hemispherically shaped to facilitate manual pumping when the flat side of the bulb 110 is positioned against a relatively rigid surface. The bulb 110 is constructed from one or more sheets formed in the desired hemispherical shape substantially in the manner described above with respect to construction of the primary bladder 54. Alternatively, the bulb 110 is formed by conventional molding techniques. In any case, the skin of the bulb 110 is typically thicker than the skin of the primary bladder 54 to provide the bulb 110 with the desired memory characteristics.

The pump outlet 66 is provided at one end of the chamber 112 in sealed engagement with the fluid-addition port 60 of the pad 50. The pump outlet 66 is in selective fluid communication with the primary bladder 54 by means of the bladder inlet 64 and injection valve 62. A pump inlet 114 is provided at the opposite end of the chamber 112 having a one-way valve 116 positioned therein to provide selective fluid communication between the chamber 112 and the external environment, but only in the direction of the pump chamber 112. The pump inlet valve 116 is preferably a check valve having substantially the same construction as the injection valve 62.

Manual operation of the pump 52 enables the addition of pressurized air to the primary bladder 54 by cycling the pump 52 through an intake mode and a discharge mode while maintaining the release valve 70 in a closed position. The intake mode begins with the user initially maintaining the bulb 110 in a compressed, flattened condition by manually squeezing it. The user then releases the bulb 110, allowing the bulb 110 to return to its memorized hemispherical shape, thereby filling the pump chamber 112 with ambient air from the external environment via the pump inlet 114 and the check valve 116 while maintaining the injection valve 62 closed. After the pump chamber 112 is fully inflated, the user initiates the discharge mode by regrasping the bulb 110 and manually squeezing it. The air pressure within the pump chamber 112 opens the injection valve 62 while maintaining the pump inlet valve 116 closed. Consequently, the air is displaced at elevated pressure from the pump chamber 112 into the primary bladder 54 via the pump outlet 66 and the bladder inlet 64. When the bulb 110 is substantially flattened, the intake/discharge cycle can be repeated as often as desired until the primary bladder 54 achieves the desired size or internal air pressure.

Referring to FIG. 11, the release valve 70 is shown to be integral with the fluid-release port 68 and is preferably positioned proximal to the pump 52 to facilitate manual adjustment of the air pressure in the lateral knee condyle pad 50 by the user. The release valve 70 comprises a valve plunger 118 biased by a spring 120 against a valve seat 122 when the valve 70 is in the closed position as shown, thereby blocking fluid communication between the interior of the primary bladder 54 and the external environment via the bladder outlet 72. The release valve 70 is placed in the open position in a manner apparent to the skilled artisan, by displacing the valve plunger 118 away from the valve seat 122 into the valve chamber 124, thereby enabling fluid communication between the interior of the primary bladder 54 and the external environment via the bladder outlet 72. Since the air pressure is typically higher in the primary bladder 54 than in the external environment, air flows out of the primary bladder 54 into the external environment, rather than vice versa, when the release valve 70 is opened.

It is readily apparent to the skilled artisan that alternate configurations of the above-described pump are possible within the scope of the present invention. For example, the pump inlet can be an unobstructed valve-free orifice that is maintained open during the pump intake mode, but is covered by the fingertip of the user during the pump discharge mode to prevent the escape of air from the pump chamber into the external environment. Alternatively, the pump can have a bellows configuration as disclosed in U.S. Pat. No. 4,378,009, incorporated herein by reference. It is likewise apparent that alternate configurations of the above-described release valve are also possible within the scope of the present invention. The release valve can be essentially any conventional valve having a selectively open and closed position, such as a gate valve, a needle valve, or the like.

It is further apparent to the skilled artisan that alternate configurations of the above-described network of pump, valves and ports are possible within the scope of the present invention. For example, the bladder outlet and bladder inlet can be integrally contained within a single unitary port. The single port is provided with a valve that enables the port to function as the bladder inlet when the valve is set in one position and enables the port to function as the bladder outlet when the valve is set in another position. It is still further apparent that by providing appropriate valving within the purview of the skilled artisan, the pump outlet and pump inlet can be placed in selective fluid communication with the external environment when the single port is functioning as the bladder outlet. It is also apparent that the pump can be coextensively constructed as an integral unit with the bladder, wherein the fluid-addition port is provided with a single opening between the pump chamber and the interior of the bladder, thereby obviating a tubular port. It is additionally apparent that although the orthopedic knee brace 28 of FIG. 2 is shown having a separate pump 52 for each pad, it is within the purview of the skilled artisan to provide an orthopedic knee brace having a single pump in selective fluid communication with a plurality of pads using a network of valves and tubing, thereby enabling selective inflation of the plurality of pads by means of the single pump simply by repositioning one or more valves.

While the foregoing preferred embodiments of the invention have been described and shown, it is understood that alternatives and modifications, such as those suggested and others, may be made thereto and fall within the scope of the present invention.

We claim:

1. An orthopedic brace positionable on a body of a user about a joint comprising:
   a substantially rigid or stiffened upper support component having an inside face positionable proximal to the body of the user above the joint;
   a substantially rigid or stiffened lower support component having an inside face positionable proximal to the body of the user below the joint;
   a hinge rotatably connecting said upper and lower support components having a substantially rigid or stiffened inside face positionable proximal to the body of the user at the joint;
   a pad having a bladder, said pad engaging said inside face of said hinge and positionable against the body of the user at the joint, wherein said bladder has a loop substantially encircling an interior opening, said loop adaptable in size to substantially circumscribe a condyle of the joint and said interior opening adaptable in size to receive a bony protrusion of the condyle, thereby alleviating pressure applied to the bony protrusion by said hinge plate; and
   a pump in fluid communication with said bladder adapted for addition of a fluid to said bladder.

2. An orthopedic brace as recited in claim 1, wherein said loop is a closed curve.

3. An orthopedic brace as recited in claim 2, wherein said loop is a partially opened curve.

4. An orthopedic brace as recited in claim 1, further comprising a fluid release valve in fluid communication with said bladder having an open position and a closed position adapted for release of fluid from said bladder.

5. An orthopedic brace as recited in claim 1, further comprising means for selectively providing fluid communication from said pump to said bladder and preventing fluid communication from said bladder to said pump.

* * * * *